(12) United States Patent
Llinas et al.

(10) Patent No.: US 7,818,065 B2
(45) Date of Patent: Oct. 19, 2010

(54) CONDUCTING POLYMER NANOWIRE BRAIN-MACHINE INTERFACE SYSTEMS AND METHODS

(75) Inventors: Rodolfo R. Llinas, New York, NY (US); Ian W. Hunter, Cambridge, MA (US); Bryan P. Ruddy, Somerville, MA (US)

(73) Assignees: New York University, New York, NY (US); Massachusetts Institute of Technology, Cambridge, MA (US)

( * ) Notice: Subject to any disclaimer, the term of this patent is extended or adjusted under 35 U.S.C. 154(b) by 775 days.

(21) Appl. No.: 11/396,340

(22) Filed: Mar. 31, 2006

(65) Prior Publication Data
US 2010/0106259 A1 Apr. 29, 2010

Related U.S. Application Data

(60) Provisional application No. 60/667,897, filed on Mar. 31, 2005.

(51) Int. Cl.
*A61N 1/00* (2006.01)
(52) U.S. Cl. .......................... 607/57; 977/762; 977/925
(58) Field of Classification Search .................. 607/57; 424/422, 486; 324/658; 514/185; 977/762, 977/925
See application file for complete search history.

(56) References Cited

U.S. PATENT DOCUMENTS

| 6,287,765 | B1 | 9/2001 | Cubicciotti | |
|---|---|---|---|---|
| 6,946,851 | B2* | 9/2005 | Lee et al. | 324/658 |
| 2001/0045547 | A1 | 11/2001 | Senecal et al. | |
| 2004/0086569 | A1* | 5/2004 | Sparer et al. | 424/486 |
| 2004/0133118 | A1 | 7/2004 | Llinas | |
| 2005/0025797 | A1* | 2/2005 | Wang et al. | 424/422 |
| 2007/0027129 | A1* | 2/2007 | Tuszynski et al. | 514/185 |

FOREIGN PATENT DOCUMENTS

EP 0337487 10/1989

* cited by examiner

*Primary Examiner*—George Manuel
(74) *Attorney, Agent, or Firm*—Foley & Lardner LLP

(57) ABSTRACT

The present invention relates to conducting polymer nanowires and their use in a brain-machine interface which is secure, robust and minimally invasive. In accordance with a first aspect of the present invention, a vascular-based brain-machine interface comprising conducting polymer nanowires is disclosed.

19 Claims, 9 Drawing Sheets

Mag= 833x  30μm  Detector= SE1
EHT= 20.00kV      Date: 10Jan2005

Polypyrrole

PF6⁻ Ions 0.5 mm

Polypyrrole 1.18 - 1.34 mm

PF6⁻ Ions 0.5 mm

FIG. 7A
FIG. 7B
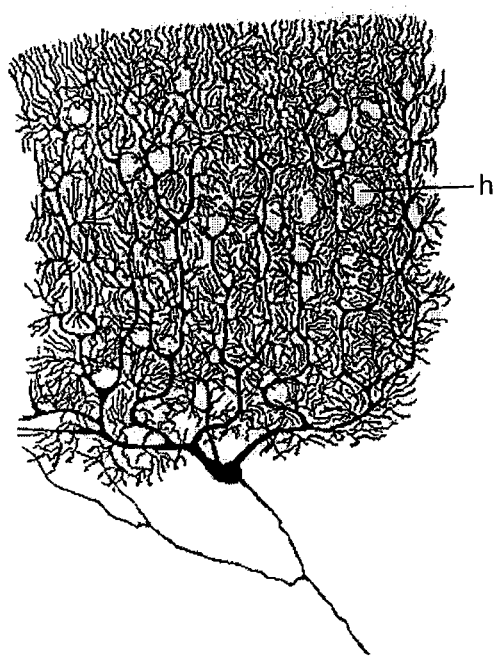
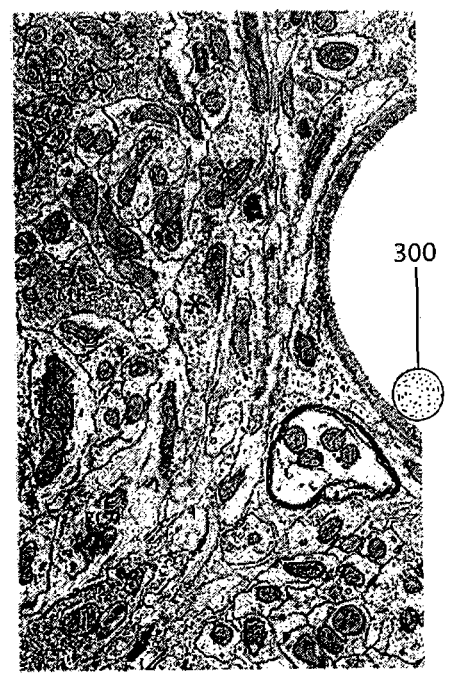
FIG. 8
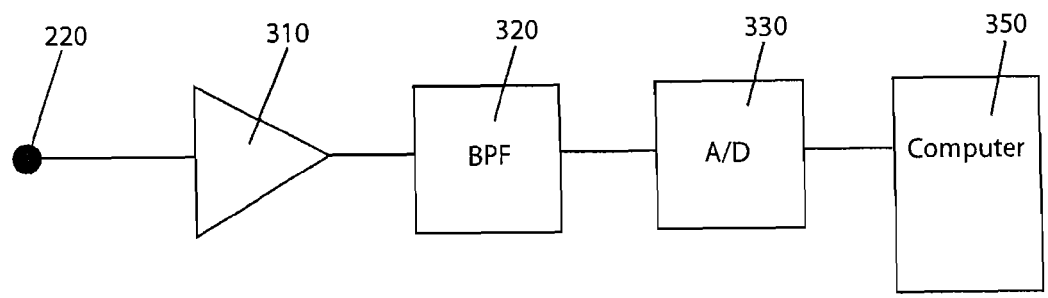

CONDUCTING POLYMER NANOWIRE BRAIN-MACHINE INTERFACE SYSTEMS AND METHODS

STATEMENT REGARDING FEDERALLY SPONSORED RESEARCH OR DEVELOPMENT

This invention was made with Government support under Grant No. CTS-0227589, awarded by the National Science Foundation. The United States Government may have certain rights to this invention pursuant to the terms of this grant.

BACKGROUND OF THE INVENTION

When considering the role of neuroscience in modern society, the issue of a brain-machine interface (e.g., between a human brain and a computer) is one of the central problems to be addressed. Indeed, the ability to design and build new information analysis and storage systems that are light enough to be easily carried, has advanced exponentially in the last few years. Ultimately, the brain-machine interface will likely become the major stumbling block to robust and rapid communication with such systems.

To date, developments towards a brain-machine interface have not been as impressive as the progress in miniaturization or computational power expansion. Indeed, the limiting factor with most modern devices relates to the human interface. For instance, buttons must be large enough to manipulate and displays large enough to allow symbol recognition. Clearly, establishing a more direct relationship between the brain and such devices is desirable and will likely become increasingly important.

With conventional means, brain activity can be recorded from the surface of the skull. In the case of electro-encephalography (EEG), electrodes are placed on the skull and record activity occurring on the surface of the brain. In the case of magneto-encephalography (MEG), recording probes are also placed on the surface, but through triangulation brain activity can be mapped in three dimensions.

Such methods as EEG and MEG, while minimally invasive, suffer from poor resolution and distortion due to the deformation of electromagnetic fields caused by the scalp and skull. To overcome these limitations with known technology requires the much more invasive option of opening the skull and inserting electrodes into the brain mass. Similarly, to stimulate the brain as is done therapeutically for some patients with Parkinson's disease or the like, the skull must be opened and electrodes inserted.

As the need for a more direct relationship between the brain and machines becomes increasingly important, a revolution is taking place in the field of nanotechnology (n-technology). Nanotechnology deals with manufactured objects with characteristic dimensions of less than one micrometer. It is the inventors' belief that the brain-machine bottleneck will ultimately be resolved through the application of nanotechnology. The use of nanoscale electrode probes coupled with nanoscale electronics seems promising in this regard.

To date, the finest electrodes have been pulled from glass. These microelectrodes have tips less than a micron in diameter and are filled with a conductive solution. They are typically used for intracellular recordings from nerve and muscle cells. A limitation is that activity is recorded from only one cell at a time. It has been possible, however, to obtain recordings from over 100 individual cells using multi-electrode arrays. Nonetheless, this is an invasive procedure as the electrodes are lowered into the brain from the surface of the skull.

In addition to probing large numbers of points in the brain, the need also exists for processing the large number of signals thus captured and analyzing them in a meaningful way. Methods for processing and displaying signals from multiple sites within the brain have been developed for multi-electrode work with animals and for MEG work with human subjects A robust and non-invasive way to tap, address and analyze brain activity that is optimized for future brain-machine interaction is disclosed, for example, in United States Published Application No. US 2004/0133118, which is incorporated herein by reference. Nevertheless, a need exists for the use of nanowires with greater biocompatibility and biodegradation thus allowing for greater brain interface. In particular, contact between blood and a biomaterial results in a rapid activation of the coagulation and complement systems. While thrombin and other activated clotting factors may be diluted under high blood flow conditions, insertion of a nanowire may alter blood flow and or cause turbulence that could promote adhesion of platelets. Although many polymers are biocompatible, not all are degradable. Degradation or dissolution changes the shape, size or mass of a polymer. While hydrolysis is the most common mode by which polymers degrade, oxidation and enzymatic, cellular or microbial degradation can also occur. Greater biocompatibility of the nanowire will result in less disruption of blood flow and will enhance the ability to tap, address and analyze the brain.

Similarly, current metallic electrodes are easily distorted or even fractured with the application of minimal force. As such, there is a need for more resistant nanowires with greater flexibility and resistance to fatigue which will withstand impact with particulates in the blood.

In addition to serving as a means of interacting with machines, a brain-machine interface could also be useful in the diagnosis and treatment of many neurological and psychiatric conditions.

Furthermore, current metallic electrodes conduct both longitudinally, as well as laterally along the axis of the wire. As such there is a need for a nanowire which can conduct longitudinally only to better direct the location of charge for the treatment and testing of many neurological and psychiatric conditions. Similarly, current electrodes lack the ability to selectively deflect along any axis and thus are limited in the specificity to which they can be directed.

The ability of polymers to act as electrical insulators is the basis for their widespread use in the electrical and electronic fields. However, material designers have sought to combine the fabrication versatility of polymers with many of the electrical properties of metals. There are instances when an increased conductivity or relative permittivity of the polymer is warranted, such as in applications which require antistatic materials, low-temperature heaters, electromagnetic radiation shielding and electric field grading. A few select polymers, such as polyacetylene, polyaniline, polypyrrole and others, can be induced to exhibit intrinsic electronic conductivity through doping, though these systems often tend to be cost prohibitive and difficult to fabricate into articles.

BRIEF SUMMARY OF THE INVENTION

The present invention relates to conducting polymer nanowires and their use in a brain-machine interface which is secure, robust and minimally invasive. In accordance with a first aspect of the present invention, a vascular-based brain-machine interface comprising conducting polymer nanowires is disclosed.

The fact that the nervous system parenchyma is permeated by a rich vascular bed makes this space a very attractive area for a brain-machine interface. Gas exchange and nutrient delivery to the brain mass occur in the brain across 25,000 meters of capillaries having diameters of approximately 10 microns. Moving towards the heart, the vessels increase rapidly in diameter with a final diameter of over 20 millimeters.

The present invention employs conducting polymers which may be synthesized through electrochemical deposition onto a conductive electrode and manufactured into conducting polymer nanowires and microwires. The conducting polymer nanowire technology coupled with nanotechnology electronics record activity and/or stimulate the nervous system, e.g., brain or spinal cord through the vascular system. The present invention allows the nervous system to be addressed by a large number of isolated conducting polymer nano-probes that are delivered to the brain via the vascular bed through catheter technology used extensively in medicine and particularly in interventional neuroradiology.

In accordance with the present invention, an exemplary embodiment of a recording device comprises a set of conducting polymer nanowires (n-wires) tethered to electronics in a catheter such that they may spread in a "bouquet" arrangement into a particular portion of the brain's vascular system. Such an arrangement can support a very large number of probes (e.g., several million). Each conducting polymer nanowire is used to record the electrical activity of a single neuron, or small group of neurons, without invading the brain parenchyma. An advantage of such a conducting polymer conducting polymer nanowire array is that its small size does not interfere with blood flow, gas or nutrient exchange and it does not disrupt brain activity.

The techniques of the present invention are also applicable to the diagnosis and treatment of abnormal brain function. Such technology allows constant monitoring and functional imaging as well as direct modulation of brain activity. For instance, an advanced variation of conventional deep brain stimulation can be implemented in accordance with the present invention by introducing a conducting polymer nanowire or bouquet of nanowires to the area of the brain to be stimulated and selectively directing a current to the area by selectively deflecting the wires and creating longitudinal conductivity.

With the present invention, intravascular neuronal recordings can be amplified, processed, and used to control computer interfaces or artificial prostheses. In controlling computational devices, neuronal activity becomes the user input, very much like the manipulation of devices such as keyboards and mice is today. Such input signals could also be used to control the movement of natural limbs that have been separated from their nerve supply through spinal cord or other injury. Thus while direct interface with "intelligent" devices can significantly improve the quality of life for normal individuals, it can also impact disabled individuals, allowing them to be more fully involved in everyday activities.

Obtaining minimally invasive recordings from the brain can also be a useful diagnostic tool in neurology and psychiatry. It provides a functional image of activity deep within the brain that could be localized with precision when combined with MRI. The arrangement of intravascular conducting polymer nano-electrodes in accordance with the present invention can also be used for localized deep brain stimulation without the current need for opening the skull. One advantage of using intravascular conducting polymer nano-electrodes for therapeutic stimulation is that the position of the stimulating electrodes can be easily adjusted. Such adjustment is difficult with the implanted stimulating electrodes used today.

A brain-machine interface based on the nanotechnology/vascular approach of the present invention also has the advantage of being retrievable in that the nano-scale conducting polymer electrodes are small enough so that even with a large number of electrodes, the interface can be removed without violating the integrity of the brain.

BRIEF DESCRIPTION OF THE DRAWINGS

Other objects, features and advantages of the invention discussed in the above summary of the invention will be more clearly understood from the following detailed description of the preferred embodiments, which are illustrative only, when taken together with the accompanying drawings in which:

FIGS. 7A and 7B illustrate a Purkinje cell of the brain and its associated vasculature;

FIG. 8 is a block diagram showing the processing of signals obtained from a nano-electrode;

DETAILED DESCRIPTION OF THE INVENTION

Figure 1A:
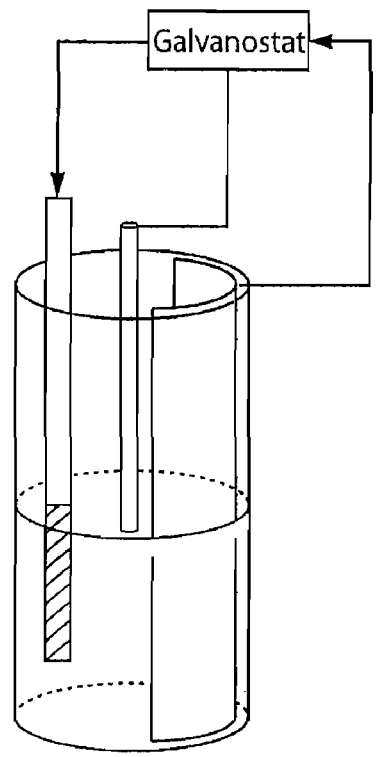
FIG. 1A is a Schematic electrochemical synthesis setup cell.

The present invention provides a conducting polymer nanowire which can be utilized in a brain-machine interface. The preparation of the nanowire may optionally comprise coating a substrate with an insulating polymer, coating the substrate or the substrate coated with insulating polymer with metallic or conducting backing layer by conventional methods, electrochemically coating the substrate or metal coated substrate with a polymer using a monomer, or a mixture of the monomer and an activator, optionally doping the pre-coated substrate with a doping agent to obtain the conducting polymer nanowire.

For most applications, the conducting polymer nanowires are typically provided with an insulating layer which extends along the length of the nanowires up to, but not including the tip portion. This can be accomplished by coating the conducting polymer nanowire with an insulator (e.g., parylene) which may be accomplished using a vapor deposition technique. In one embodiment, a 100 nm layer of parylene is used which is sufficiently thick such that it does not have pinholes and is adequate to insulate the conductive material. The parylene coating may be removed from the tip portion using laser ablation in order to expose the underlying conducting polymer.

With the tip of the conducting polymer nanowire exposed (i.e., any insulator removed), the tip area may be further processed in order to enhance or diminish certain properties of the tip region of the nanowire. As an example, the exposed tip region may have a length which is roughly on the order of the diameter of the nanowire. Thus, if the nanowire has a diameter of 10 μm, then the exposed tip region may have a length which is in the range of 1-20 μm. The processing of the tip region may be selectively performed in order to control the properties of the nanowire tip region. For example, the electrical conductivity of the tip region may be increased or decreased by adding certain material to the tip region. Also, certain materials may be added in order to increase or decrease the affinity of the tip to certain chemicals or materials.

At the tip region of the conducting polymer nanowire, the individual strands of material making up the nanowire are typically "frayed" similar to the individual strands making up a rope. This "fraying" may or may not affect the diameter of the nanowire at the tip region. In some instances, there may be hardly any increase in nanowire diameter, while in other instances there may be an increase in nanowire diameter on the order of 50%. If there is an increase in nanowire diameter, the nanowire may be selectively "shaved" or trimmed, using, for example, a microtome blade or a laser trimming process.

The "fraying" at the end of the nanowire essentially creates pockets or openings which serve to increase the exposed surface area of the material making up the nanowire. This increased surface area at the tip region of the nanowire may then be subjected to an electrochemical dip or growing process in order to selectively add another material at the tip region. The particular material is added based on the enhancement or function which is desired to be achieved. For example, if it is desired to increase the conductivity of the tip region of the nanowire, then platinum is added to the tip region. The material to be added to the tip may be added in a number of different ways. For example, such processes may include electrolytic deposition, electroless deposition, or vapor deposition, such as electron beam deposition.

If a metal is added to the tip region, an optional subsequent step may be to turn the metal into a metal salt. This may be achieved, for example, by electrochemically converting the metal into a metal salt. For example, in the case of a metal such as silver which is deposited on the nanowire, the silver may be electrically converted to silver chloride through the use of electrical current, as is well known in the art.

As an alternative to providing an insulating outer layer, the conducting polymer nanowires which are used in the present invention may be fabricated in such a way that they are electrically conductive only in the longitudinal direction, exhibiting such oriented conductivity due to the molecular structure of the polymer chain making up the nanowire. As such, there is practically no electrical conductivity in the radial direction, with the longitudinal conductivity being up to 10 orders of magnitude or more than that in the radial direction. In the case of such polymer nanowires, there is no need to provide a separate insulator layer since there is no electrical conductivity out of the sides of the wire.

Conducting polymers for use with the present invention include, but are not limited to, polymers synthesized from monomers, biopolymers, and doped insulating polymers. The monomer used for producing the conducting polymer wires is selected from the group consisting of aromatic or heterocyclic compounds containing nitrogen such as aniline, pyrrole, 3-methyl pyrrole, anisidene and toluediene. Preferred conducting polymers include, but are not limited to, polyacetylene, polyaniline, polypyrrole, polythiophene, and polyethylene dioxythiophene (polyEDOT). In a preferred embodiment, conducting polymers can be produced so that their conductivity shows metallic behavior, although they contain no metallic elements. It is believed that the conductivity of these polymers is a result of the strong σ bonds as well as the delocalization of electrons through the common conjugated π bonds. Charge transport inside the polymer takes place both along the polymer backbone (intrachain transfer) as well as between chain (interchain transfer)

In preferred embodiments, the conducting polymer is n-doped or p-doped. By adding doping elements to relatively insulating polymers, such as polyacetylene, high intrinsic conductivities can be obtained. By adjusting the type and level of dopant used, the conducting polymer can be synthesized so as to possess conductivities in the range of $10^3$ to $10^9$ S/m. Suitable doping elements include $Br_2$, $Cl_2$, $I_2$, and $AsF_5$. As dopants are added to the polymer, electrons or holes have to be injected to maintain charge neutrality. Doping may preferably be achieved chemically, electrochemically or through photon absorption as the polymer is being synthesized or after synthesis is complete.

In some embodiments the doping level can be chemically or electrochemically switched using standard methods. The switching of doping level can dramatically affect the conductivity of the conducting polymer wire giving more control over the charge in the polymer wires after incorporation into the brain-machine interface. In preferred embodiments, the doping level can be switched continuously from a semiconductor to a conductor (metal) via an electrical signal. The process is schematically depicted below:

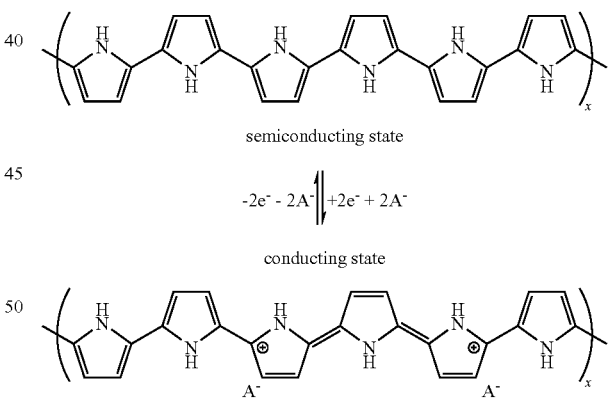

As doping levels are switched, properties such as color and volume can be adjusted. For example, volumetric changes can be obtained by switching the doping level of polypyrole or polyEDOT. The doping is optionally done when the polymer synthesis is carried out only with the use of the monomer.

Figure 4A:
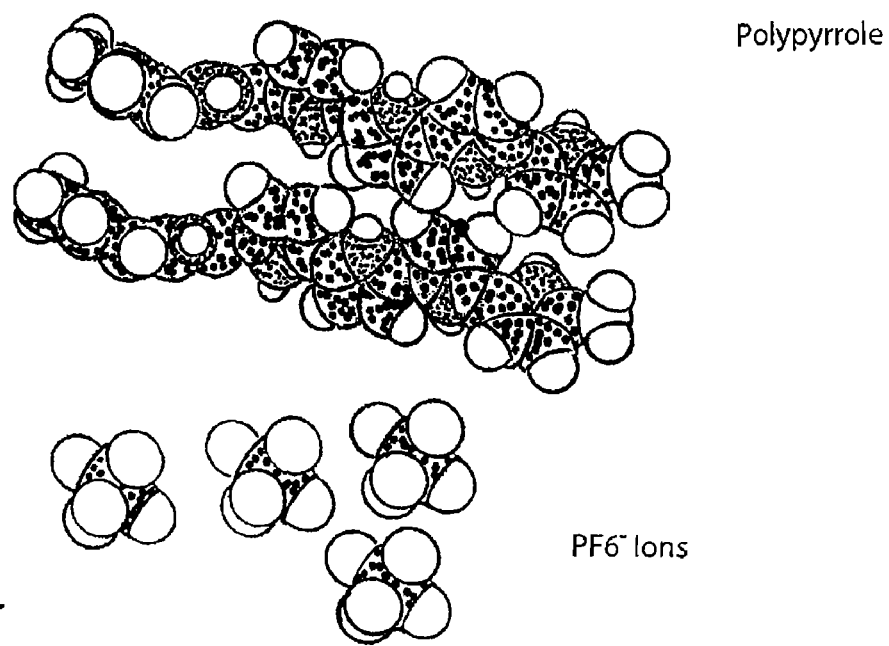
FIG. 4 is a molecular space-filling model of the electrochemical red-ox cycle for polypyrrole in which A represents the reduced state and B represents the oxidized state.
Figure 4B:
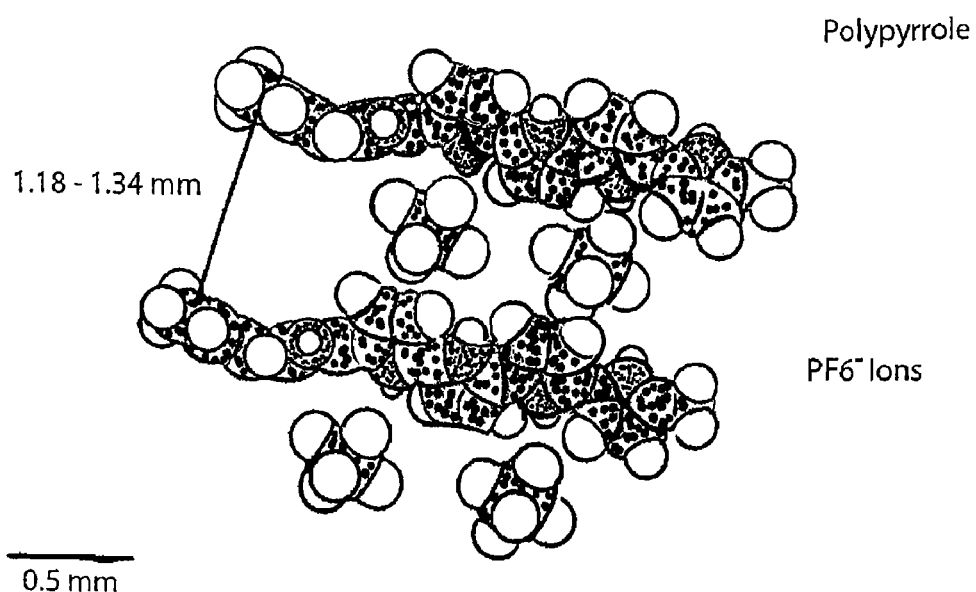

In a preferred embodiment, the doping is either permanent or reversible. When the doping is reversible, conducting polymer transistors with electrochemically controllable resistance can be produced. A molecular space filling model of the red-ox cycle for polypyrrole can be seen in FIG. 4.

Conducting polymers can be synthesized via electrochemical deposition onto a conductive electrode. Electrochemical polymerization allows precise control of polymer growth via the amount of electrons passed through the electrical circuit. The reaction taking place at the working end of an electrode is shown below, in this example for polypyrrole:

The details of fabricating conducting polymer nanowires may be found, for example, in U.S. Pat. Nos. 6,249,076; 6,157,113; and 6,084,321, the contents of which are collectively incorporated herein by reference.

Figure 1B:
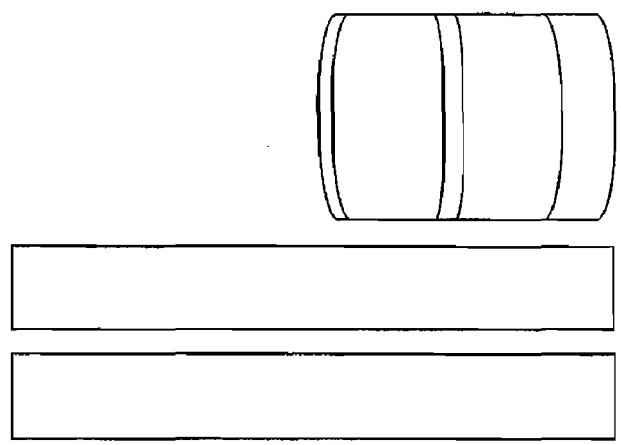
FIG. 1B is the resulting polypyrrole film showing the crucible side of the polypyrrole films.
Figure 1B:
Figure 2A:
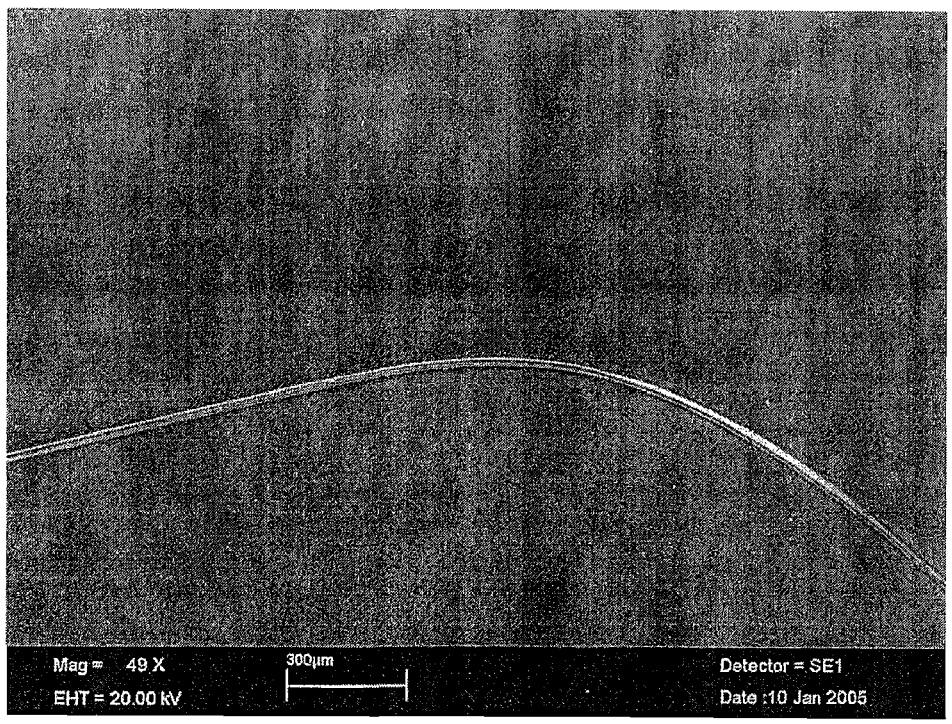
FIG. 2A is an electron micrograph of a conducting polymer microwire having a 15 μm square cross-section with a total length of 20 mm.
Figure 2B:
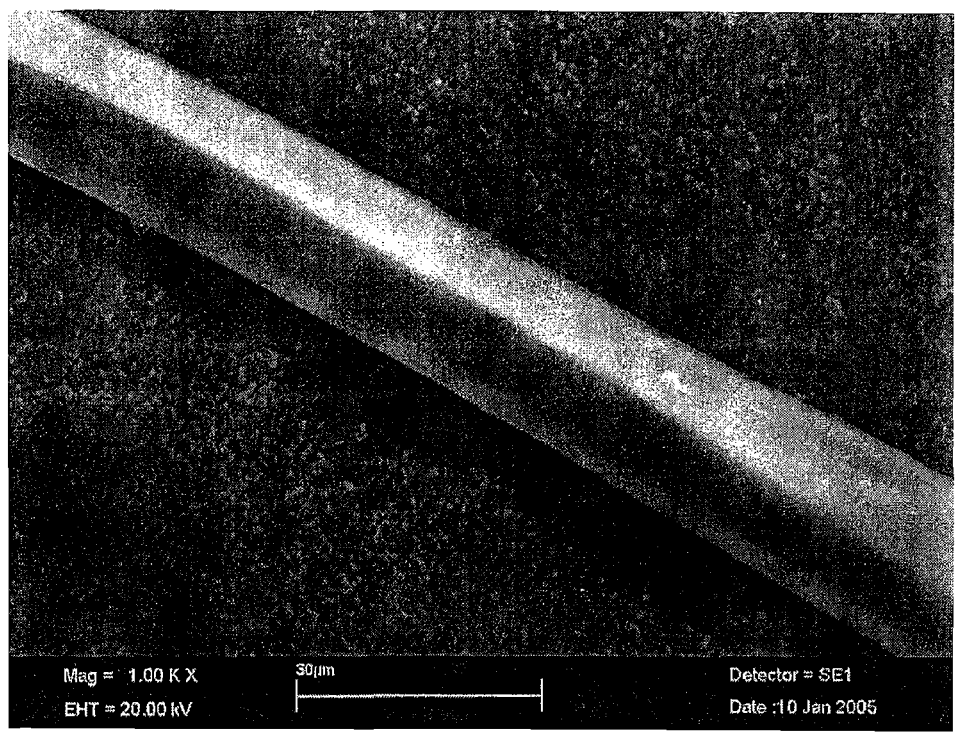
FIG. 2B is an electron micrograph of a close up image of a conducting polymer microwire having a 15 μm square cross-section with a total length of 20 mm.
Figure 2C:
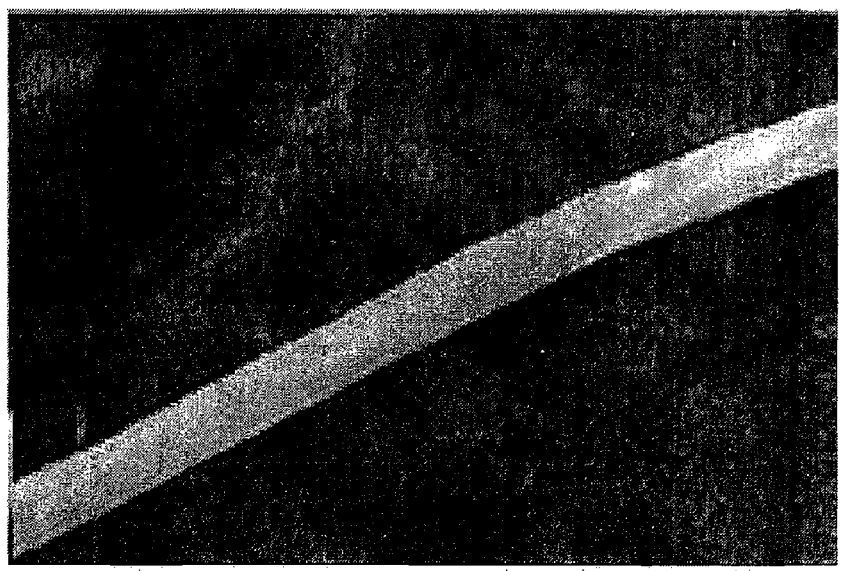
FIG. 2C is an electron micrograph of a conducting polymer microwire having a 15 μm by 2 μm cross-section.

The counterion is incorporated at the time of synthesis and is intercalated between the polymer chains. Polymerization is believed to occur via chain grown coupling of oxidized monomers in radical cation form. Once the solubility limit is reached, the polymerized oligomers precipitate out of the solution onto the working electrode. A schematic of the electrochemical synthesis cell can be seen in FIGS. 1A and 1B. The conducting polymer nanowires and microwires are manufactured via slicing electrochemically grown polymer films. An example of these wires can be seen in FIGS. 2A, 2B and 2C.

In one embodiment, conducting polymer nanowires are produced by coating polymer fibers of the appropriate dimensions with a conductive material. In a preferred embodiment, the polymer fibers to be coated with a conducting polymer material are electrospun polymers or carbon nanotubes. In a further preferred embodiment, the fiber template is at least about 1 mm long and less than about 1 μm in diameter.

When the polymer fiber template is made from electrospun polymers, a wide range of polymers can be used. In particular embodiments, the electrospun polymers are synthetic polymers including, but not limited to, polyacetylene, polyaniline, polypyrrole, polythiophene, and polyethylene dioxythiophene (polyEDOT) or biopolymers, including but not limited to silk. Silk insulated conducting polymer wire can be produced by chemical polymerization on the fiber in solution or in vapor using standard techniques. Due to its properties as a strong yet biocompatible polymer, silk is a particularly preferred substrate.

When the polymer fiber template is made from carbon nanotubes, the carbon nanotubes can be produced by spinning, lithographic patterning or the use of individual large-diameter nanotubes using standard techniques. Carbon nanotubes are particularly preferred for permanent applications by providing a strong and highly conductive template. In a preferred embodiment, carbon nanotube conducting polymer wires are produced by electrodepositing the desired polymer on the fiber and subsequently applying an insulating coating Conducting polymer microwires or nanowires may be produced by slicing a free-standing conducting polymer film. There are a number of ways to prepare such films, and a number of ways to slice them. The films may be polypyrrole films which can be produced by electrodeposition in a two electrode cell. Glassy carbon is used as the anode, and copper as the cathode. The cell is filled with a propylene carbonate solution, containing 1% (vol.) distilled water, 0.05 mol/L pyrrole, and 0.05 mol/L tetraethylammonium hexafluorophosphate, that has been chilled to −40° C. A polypyrrole film forms on the anode as current is passed through the cell. The resulting film typically has a thickness between 5 μm and 50 μm, with the particular thickness being achieved by varying the current density at the anode and the total deposition time. Other types of conducting polymer films may be prepared by spin casting, drop casting, rolling, electroless deposition, or other processes well known in the art.

The microwires or nanowires are prepared from the polypyrrole films. In one exemplary embodiment, the polypyrrole film is cut into a piece approximately 2 cm by 2 cm. A small rectangular container is filled halfway with distilled water, and the piece of polypyrrole film is floated on the surface of the water. The container is then placed in a freezer until the water is fully frozen. A layer of distilled water is added on top of the polypyrrole film and ice, and subsequently frozen. The resulting block of ice is then freed from its container, and fastened to a cryo-microtome stage with embedding compound such that the polypyrrole film is oriented perpendicular to the stage.

The mounted polypyrrole film is then sliced on a cryo-microtome (for example, UltraPro 5000 available from Vibratome, St. Louis, Mo.). In an exemplary embodiment, the section thickness is chosen to equal the film thickness, so as to produce square cross-section wires. Of course, it should be understood that any thickness and any cross-section shape may be selected, depending on the particular application and the type of microwire or nanowire it is desired to produce. The wires are collected from the microtome on glass slides, warmed to room temperature, and dried. Insulation may be selectively applied in the form of a dichloromethane solution of poly(ethylene oxide), which is allowed to evaporate.

In a further embodiment, conducting polymer nanowires are produced using conventional plastic processing techniques. In particular, many conducting polymers that are soluble in organic solvents and can be melt-processed and can be utilized by the current invention. These processable materials include, but are not limited to polyaniline, substituted polythiophenes, and substituted polypyrroles. In preferred embodiments, the processable material may be less conductive while still maintaining adequate conductivity for the brain interface applications. In other preferred embodiments, the processable material may be less processable than other materials yet maintain higher potential for biocompatibility. In one embodiment, intelligent nanostructured scaffolds can be created by covalent attachment of the laminin adhesive peptide, YIGSR, onto the surface of polyaniline films/fibers and into the polymer structure during synthesis.

In one embodiment, conducting polymer nanowires are produced by drawing the processable materials from a preform, similar to the production of an optical fiber. Drawing the nanowires from a preform yields repeatable feature sizes. Using a fiber drawing technique can produce a complex conducting polymer wire preform with multiple conductors and/or shielding which can be drawn down to the desired size. In one embodiment, the nanowires produced by the fiber drawing technique comprise a removable filler material, including but not limited to, carbon black, graphite, metallic particles, carbon fibers, intrinsically conducting polymers, fullerenes, carbon nanotubes and mixtures thereof. In another embodiment, the preform drawn nanowires comprise multiple wires within the drawn wire. Preform drawn nanowires can optionally be provided from conducting polymers with a processable precursor. For example, poly (p-phenylene vinylene) (PPV) can be prepared during thermal conversion of poly[p-xylene-alpha-dimethyldulfonium chloride]; PXDMC. These processable precursors can be converted from insulating precursors to conductive polymers using standard methods. For example, upon heating PXDMC above 115° C. an elimination reaction occurs converting the precursor to a conductive polymer. In a preferred embodiment, conducting polymer nanowires are produced by the fiber drawing technique such that the wires have a varying diameter.

Due to the solubility of conducting polymers, conducting polymer nanowires can be fabricated by core-shell electrospinning. In core-shell electrospinning, a conducting polymer is used as the core of a jet of an insulating electrospinnable fluid, with the resulting nanowire having a conducting polymer core with an insulating coating. The electrospun fiber can be directed at a rotating drum electrode to produce a continuous long nanowire. The insulating material can be dissolved in an appropriate solvent to allow for external connection and tip modification.

Figure 3:
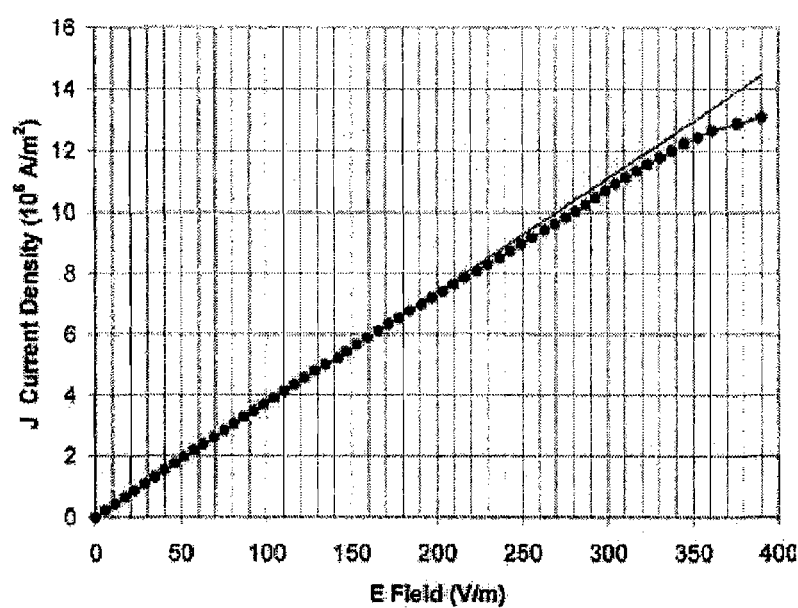
FIG. 3 is a graph representing the current density flowing through a conducting polymer wire as a function of the electric field over a large range of electric fields.

In a preferred embodiment, the nanowires of the invention have varying diameters in the range of 100 nm to 1 mm for use in brain-machine probes. Nanowires of the invention can be used at a variety of voltages. The nanowires are capable of withstanding voltages in excess of 160 V, and preferably 0 to 100 V for biological applications, without degradation. Referring to FIG. 3, therein is illustrated a graph representing the current density flowing through a conducting polymer wire as a function of the electric field over a large range of electric fields.

The conducting polymer nanowires of the present invention exhibit increased flexibility, biocompatibility and steerability. Biocompatibility is influenced by several factors including the free energy at the solid/liquid interface, the hydrophobic/hydrophilic character of the surface, and the surface chemistry/charge density. Neutral polymers and polyanions appear to be less cytotoxic than polycations. Polymer flexibility, surface roughness, and molecular weight have also been shown to influence biocompatibility. Low molecular weight polymers absorb less protein and display less platelet adhesion (See, e.g., Wang, *Pharm. Res.* (2004) 21, 1362-1373)

More particularly, the conducting polymer nanowires can be utilized in a neurovascular interface method and system which entails several aspects described herein including: (a) the determination of optimal trans-vessel recording conditions; (b) techniques for introducing and guiding conducting polymer nanowires within vessels; (c) techniques for fixing nanowires in position within vessels; (d) the acquisition of data to aid in the design of the nanowires; and (e) the determination of the optimal characteristics for recording nanowires, pre-amplifiers and amplifiers, signal processing and other ways of optimizing the collection and recording of signals. The conducting polymer nanowires of the present invention allow for the coupling of electrical stimulation and cell growth and modulation.

The conducting polymer nanowires of the present invention have superior resistance to fracture in the brain nanowire application. Malleable materials such as gold or platinum will deform with minimal forces. Conducting polymers are not malleable and thus more resistant to deformation due to impact with blood particulates.

In accordance with a first exemplary embodiment, trans-vascular electrical activity from the enteric nervous system (ENS) is recorded. Functionally, the ENS is similar to a simple brain in that it is capable of intrinsic reflex responses as well as rhythmic activity. Thus, a variety of activities can be recorded in the ENS.

Figure 5:
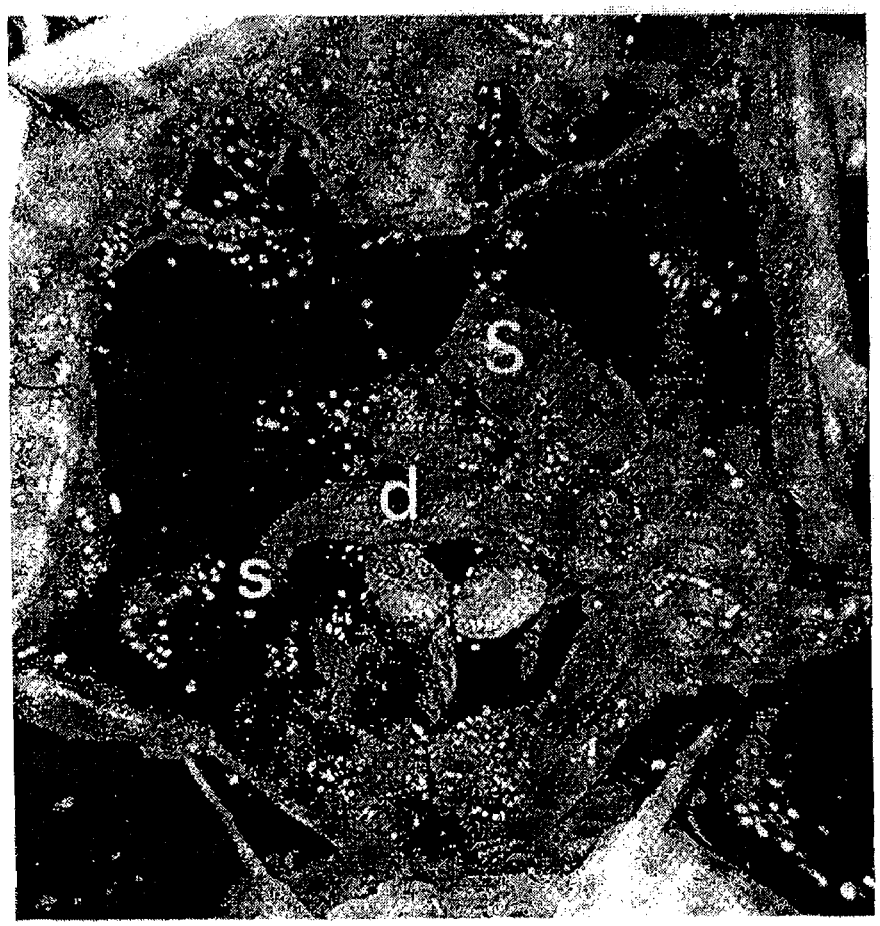
FIG. 5 shows part of the alimentary canal and mesentery of a frog, in situ.

Anatomically, the ENS and its blood supply are readily accessible. In particular, the innervation of the small intestine is particularly favorable. In mammals, the superior mesenteric artery emerges from the midline of the descending aorta at the level of the kidneys. As the artery descends, it branches off into numerous mesenteric branches which form a latticework of anastomotic loops. Straight arteries (arteriae rectae) course off from the loops and enter the small intestine. Referring to FIG. 5, therein is illustrated part of the alimentary canal and mesentery of a frog, in situ.

Each electrode array comprises a very large number of insulated conducting polymer nano-wires of different length. The diameter of each electrode can be 0.1-10 μm. In an exemplary embodiment, the number of conducting polymer nano-wires having diameters of 0.5 μm that can be deployed via a catheter having a diameter of one millimeter is approximately 3 million.

Figure 6:
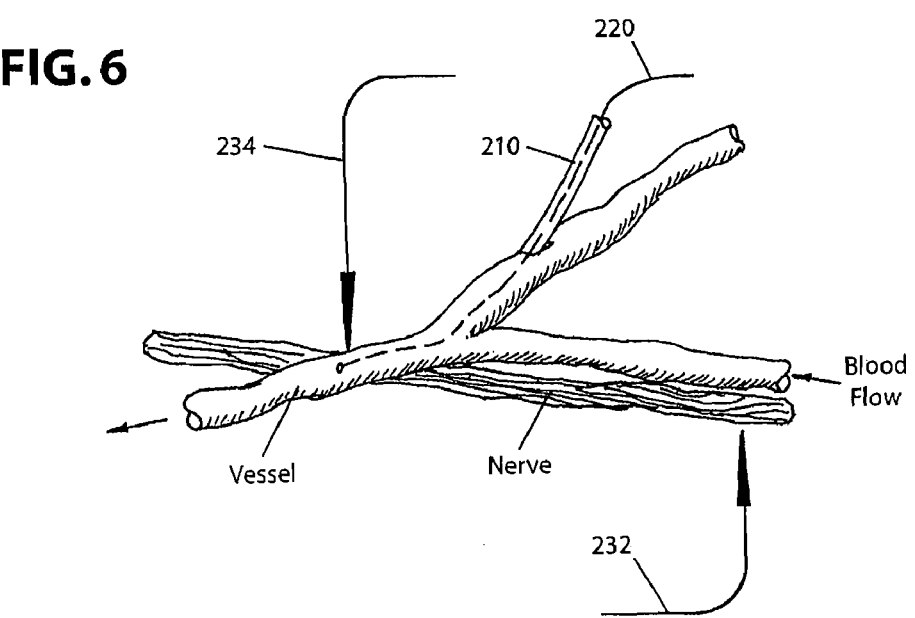
FIG. 6 illustrates the placement of a nano-electrode in vasculature proximate to a nerve fiber whose activity is to be monitored.

Each conducting polymer nano-wire within the array preferentially ends in a small, bare, cup-like enlargement which provides electrical contact with the surrounding fluid and acts as a "sail" to help move the electrode within the body, e.g., within the vascular network. The optimal size and design geometry of the electrode head depend on the forces acting on an electrode in vessels of different diameters. Once the electrodes are in the blood vessel, they are carried by the blood stream until they extend to their full length. Referring to FIG. 6, therein is illustrated the placement of a nano-electrode in vasculature proximate to a nerve fiber whose activity is to be monitored.

The smallest vascular elements, the capillaries, are significantly larger (15-25 μm) diameter) than conducting polymer nanowires (0.1-10 μm). As such, resistance to movement within small arteries and arterioles is minimal. Although blood pressure decreases with distance from the heart, it should provide adequate pressure to move the nanowires into place. In large blood vessels, closer to the heart, the pressure drastically pulsates with each heart beat and blood velocity is maximal. As vessel diameters decrease with increasing distance from the heart, the total area of the vessels sharply increases. The flow becomes laminar and slow. As such, the blood current through the free vessel branch can be viewed as being relatively constant.

To provide a sense of the size of electrodes involved in the interface of the present invention, FIGS. 7A and 7B illustrate an exemplary neuro-vascular structure in the brain and a nano-wire electrode therein for comparison purposes. FIG. 7A shows an individual Purkinje cell with its characteristic dendritic tree of neurons which is penetrated by multiple capillaries (h) (at least 20 in this case). FIG. 7B shows an enlarged detail view of a portion of FIG. 7A showing a nanowire 300 having a diameter of 0.9 μm) within a capillary of the Purkinje cell.

Fluid in the vasculature proximate to innervation tends to be electrically charged since the walls of very small vessels have relatively large openings (i.e., approximately 5% of the cross-sectional area of the vessel) and are penetrable by ions. The blood plasma and extracellular fluid are in ionic and osmotic equilibrium as water and ions move freely between these two compartments through capillary pores. As such, the electrical potential in a vessel is similar or reflects the electrical potential outside of the vessel. This allows the recording of the electrical activity of a nerve fiber or a neuron using a conducting polymer nanowire installed in a nearby vessel. In a preferred embodiment, the conducting polymer nanowire can be steered to a plurality of nearby vessels for greater accuracy.

Larger vessels contain both muscle and fibrous tissue that impede the flow of ions through the vessel walls. (Smooth muscle in large arteries may also generate a low amplitude electrical signal.) Thus, the amplitude of the neural electrical signal should increase as the electrodes move from arteries to arterioles to capillaries. By releasing several conducting polymer nanowires of different lengths in a vessel, recordings can be recorded from several points. Signals from the nanowires are then amplified and processed and can be recorded and analyzed. These signals can also be compared to those made using traditional extracellular wire ball electrodes placed near the nanowires. This helps to determine the maximum distance from a nerve at which signals can be robustly recorded intravascularly.

The directed electrical signals are in analog form and must be converted to digital form for further processing. Referring now to FIG. 8, this is accomplished using an analog-to-digital converter (ADC) 330. Prior to the analog to digital conversion, the received signal may first by amplified by amplifier 310 and filtered by way of band pass filter 320. A single ADC may be multiplexed to several electrodes. The digital output of the ADC 330 may then be provided to a computer 350 for further processing, as explained herein. For simultaneous sampling, each channel has its own amplifier and sample-and-hold multiplexed into an ADC. For higher speed, each channel may be independent, using a common clock and multi-channel memory. While a single channel may operate well, the performance of such an arrangement while many channels are active simultaneously with high frequency signals can deteriorate drastically due to channel crosstalk. This is a concern among multiple conducting polymer nanowire signal paths particularly with increasing numbers of electrodes and decreasing electrode size. There are commercially available analog input modules that are multi-channel. Because the probability of many simultaneous active channels is relatively low, such an arrangement is adequate for most situations. To further enhance performance, the analog circuitry for each individual channel should be isolated from the digital circuitry.

For a slow moving signal in a noisy environment such as may be expected in the present invention, an integrating ADC may be best. Integrating ADCs are effective in reducing 50/60 Hz noise but have a low conversion rate. The most popular converters are the successive approximation type which are available up to 100 MHz, with 12-bit resolution. High-speed programmable logic devices, besides providing the ability to synchronously address the module, are capable of accounting for any pipeline delay.

Another popular type of converter is the sigma/delta type, which uses a single bit ADC and a very high clock speed that is pipelined. Sigma/delta ADCs can have resolutions in excess of 24 bits and are very noise insensitive.

The amplifier signal inputs can be single-ended or differential. The choice depends largely on the type of noise environment in which the system will operate. In a preferred embodiment, differential inputs are used because they provide better common mode noise rejection but generally require more complex and larger circuitry. Because of their small diameters, the resistance of the nanowires is significant (e.g., 100 Ohms to 10 MOhms). As such, special care should be given when matching impedances between the electrodes and the signal inputs of the amplifiers.

The amplifiers used with the present invention should have a sufficiently wide bandwidth to insure that they can track the signal to be monitored. In a preferred embodiment, the bandwidths are in the range of 0 to 100 KHz. The sampling clock frequency for the ADC should be at least twice the amplifier bandwidth.

Because the environment in which the system of the present invention operates is generally noisy, input filters are used to improve overall performance. Hardware and/or software filters may be used. The optimal filtering depends on the nature of the noise and its characteristics. In light of the typical frequencies of the signals of neuronal activity, phenomena with frequencies above 100 KHz are generally considered noise and are to be filtered out.

Noise manifests itself as random fluctuations of the local field potential that finally produce some undesirable impact on the signal measured by the electrode. Furthermore, any time that a signal is processed or transferred in any way, noise is introduced. Typically, the noise inherent in the inhomogeneous nature of the environment surrounding an electrode is the most difficult to eliminate.

Noise in the system can be subdivided into two categories: noise inherent to the signal, and noise caused by the external environment. Inherent noise response signals are usually caused by an inhomogeneous and varying environment (e.g., flowing blood), noisy stimulus signals, or some other sources of noise within the test and measurement apparatus itself. Another source of inherent noise is due to the electrode contact potential that exists whenever metallic electrodes interface with a specimen via an electrolyte, as is the case in the environment of the present invention. The random variation of this potential is a source of noise. Statistical analysis of this noise can be used to determine an appropriate compensatory measure. External noise is generated outside the test and measurement equipment by sources such as stray electric or magnetic fields, poor shielding or grounding, poor circuit design, noisy power sources, and over-amplification.

Unless eliminated, inherent noise will be amplified along with the signal. Hence, it is desirable to eliminate it at the initial stages of signal processing. Selective filtering can be employed for this purpose. For example, to eliminate high frequency noise, a frequency window may be created by using band-pass filtering with appropriate cut-off frequencies and roll-offs to essentially create a low pass filter.

To eliminate so-called common-mode noise (e.g., noise due to power supplies generating electromagnetic waves with a frequency of 50 or 60 Hz) a differential signal may be measured using two electrodes. The differential signal may then be input to a differential amplifier. Common-mode noise can be much stronger than the measured signal. When two inputs are used, a differential amplifier will essentially subtract out the common mode noise present on both inputs and will thus amplify only the true signal.

An important factor that determines a system's tolerance for noise is the amount of noise in the measured signal, i.e., the signal-to-noise ratio (SNR). The SNR is a measure of signal strength relative to background noise. If the incoming signal strength is $V_s$ (usually on the order of millivolts) and the noise level is $V_N$, then the signal-to-noise ratio, in decibels, is:

$$SNR = 20 \log_{10}(V_S/V_N)$$

If $V_S = V_N$, then SNR=0. In this situation, the signal borders on being unintelligible because the noise level severely competes with it. This will cause strong randomness in data and consequently problems in all of the signal processing operations. Ideally, $V_S$ should be much greater than $V_N$ so that the SNR is a large positive number. As an example, for $V_S=10.0$ millivolts and $V_N=1.0$ millivolt, SNR=20 dB, which results in the signal being rather clearly discernable for most applications. If the signal is much weaker but still above the noise, e.g., 2.0 millivolts, then SNR=6 dB, which is a marginal situation. The lower the signal to noise ratio is, the greater the computational effort needed to recover the signal (with some level of errors).

There are several methods of measuring SNR. In an exemplary method employing an oscilloscope with a bandwidth of 10 MHz, one connects the output from an electrode (after amplification) to be checked and views the "black level" of the signal. The black level should be measured without any external stimulation applied. This represents $V_N$, the noise signal.

The signals recorded by the nanowires represent physical variables (currents or voltages) changing in time with respect to the dynamics of the corresponding nerves. As such, the following factors should be taken into account to optimize the performance of the present invention. First, not all electrodes will be placed at the "right" positions, i.e., some electrodes may be far enough from any neuron so as to be unable to produce reliable data, while others may be damaged. Secondly, two electrodes placed in the vicinity of a single neuron, but at different distances from the neuron will produce different output voltage traces of different amplitudes representing the behavior of the same neuron. Thirdly, the signal to noise ratio may not be optimal if an electrode simultaneously records the activities of more than one neuron.

Figure 9A:
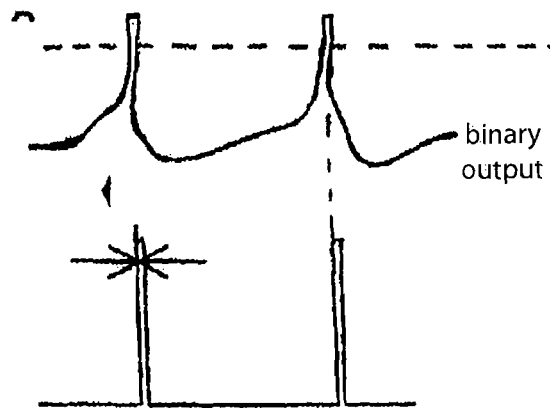
FIGS. 9A and 9B show the neuronal membrane potential as captured and as processed in accordance with the present invention, for a resting and an active state, respectively.
Figure 9B:
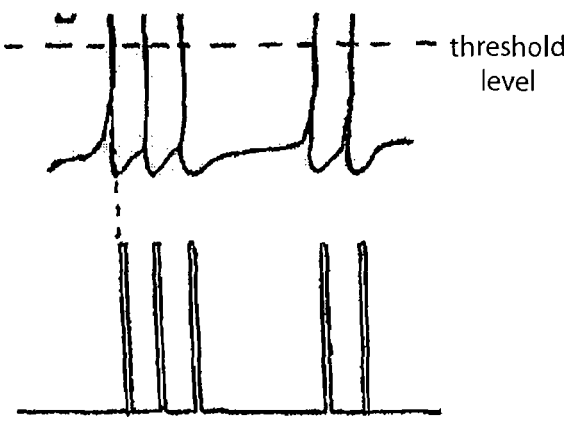

The present invention provides a method of processing the signals captured by the nanowires which provides excellent noise performance while also addressing the burdens of dealing with very large numbers of signals. To this end, in an exemplary embodiment of the present invention, the analog output signals of the nanowires are converted into binary form as follows:

1, if $x_n(t) > x_{thr}$ $\|t - t_{j-1}\| < \tau$
$x^{bin}_n$ bin(j)=0, otherwise where $t_j$ is the time of the beginning of the pulse, $x_n(t)$ is the time signal of electrode n, $\tau$ is the duration of the output pulse (i.e., the digitized signal), and $x_{thr}$ is a threshold level which if exceeded by the input signal $x_n(t)$ will cause the generation of an output pulse. By appropriately choosing the threshold level, $x_{thr}$, the influence of noise is significantly reduced. Furthermore, the problem of dealing with widely varying signal amplitudes is eliminated. The duration $\tau$ of the digitized pulses may be fixed (e.g., 5 ms). The processing represented by the above expression is illustrated in FIGS. 9A and 9B. A hardware implementation of a binary conversion scheme is described more fully below in connection with FIGS. 10B and 10C.

Electrodes which do not exhibit activity beyond a given time period (e.g., 10 sec.) can be ignored. Moreover, the analysis of binary as opposed to analog data provides processing and storage advantages. For example, memory usage is significantly reduced as is computational complexity and time. This is particularly significant in light of the large number of signals to be processed. Furthermore, for purposes of studying action potential dynamics, such a binary representation of neuronal activity should be sufficiently accurate. The different behavioral neuron states produce different firing rates. Because neurons appear to communicate with each other primarily via action potentials, the above simplification is reasonable, without unduly discarding useful signal content.

Figure 10A:
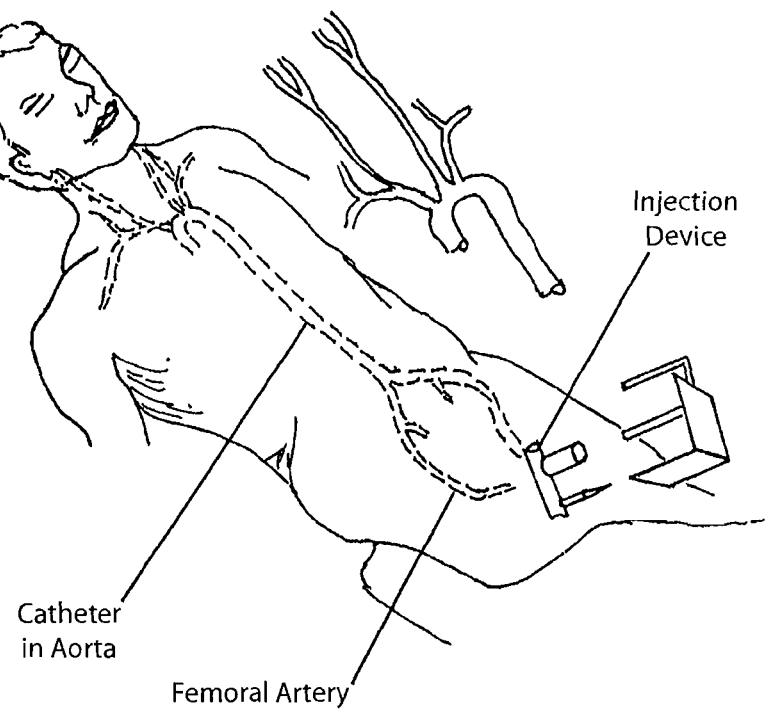
FIGS. 10A through 10C illustrate an exemplary catheter insertion procedure and device in accordance with the present invention.

FIG. 10A illustrates a conventional catheter insertion procedure that can be used to deploy an interface device in accordance with the present invention. As shown in FIG. 10A, a catheter is introduced into the femoral artery and is pushed up to a vascular territory to be addressed. The catheter may also be inserted into the carotid or the sub-clavial artery. Such a procedure is similar to interventional neuro-radiology techniques where catheters are guided to any portion of the central nervous system.

Once an area to be monitored or stimulated is reached, a set of leads held inside the catheter head are allowed to extend and become randomly distributed into the brain's circulatory system. Since a catheter can be placed in any major brain vessel, the maximum length of the nano-wire electrodes required to reach any capillary bed is on the order of 2 to 3 cm. Hence a large number of electrodes can cover any region of the central nervous system from the parent vessels harboring the stem catheters.

The present invention may also be used in connection with cochlear implants. In pathological conditions when hair cells are damaged and do not generate electrical pulses to be sent to the brain, no sound is perceived. Under this condition there always exist some residual nerve fibers in the inner ear that can be addressed with local electrical stimulation. Cochlear implants attempt to utilize these residual fibers by replacing the function of the hair cells with direct electrical stimulation. An implant system includes an external speech processor and headset and an internal, surgically implanted electrode array. These elements are connected to a set of cochlear implantable metal electrodes, usually platinum iridium alloy insulated with silicon rubber.

The conducting polymer nanowires of the present invention may be used as the electrical signaling system, replacing the larger metal wires presently utilized. The advantage afforded by the using conducting polymer nanowires in accordance with the present invention is the ability to design the electrical flow in the cochlea to one resembling the physiological distribution of current by the hair cells. This can be done because the number of polymer electrodes that may be implanted, given their small diameter can be one hundred to one thousand as many as the number of metal electrodes presently used. Thus, many more electrodes may be used and they may be positioned in different locations in order to provide better coverage and signal distribution. The advantage of the increased number of electrodes is the fact that rather than a point source for current flow the electrical charge can be regulated in space to have shapes other than the simple electrical dipole produce by a single cable system. The electrodes are distributed in the cochlea according to the place coding use by the cochlea to separate low from high frequency sounds. The electrodes may be placed to create a complex current flow geometry which facilitates sophisticated sound perception to include music nuance appreciation. In addition, the very graded staggering of tip location of the implanted wire can facilitate optimal conductor selection, minimizing the energy required for acoustic nerve stimulation and for specificity of sound perception. In the case of cochlear implants, the nanowires are effectively positioned in an extravascular location, as opposed to the transvascular or intravascular approach utilized in connection with other applications.

The present invention may also be used in connection with natural limb control or artificial/prosthetic limbs. In the case of natural limb control, particularly where nerves pathways between the natural limb and the brain have been severed or are no longer functional, the conducting polymer nanowires of the present invention, along with appropriate control/interface electronics may be used as a sort of alternate electrical pathway to convey signals between the brain and the natural limb, for example the muscles associated with the natural limb.

In the case of artificial/prosthetic limbs, the conducing polymer nanowires of the present invention may be used as an electrical pathway between the brain and the control/interface of the prosthetic limb in order to convey signals between the brain and the artificial/prosthetic limb in order to properly operate and control the artificial/prosthetic limb.

Figure 10B:
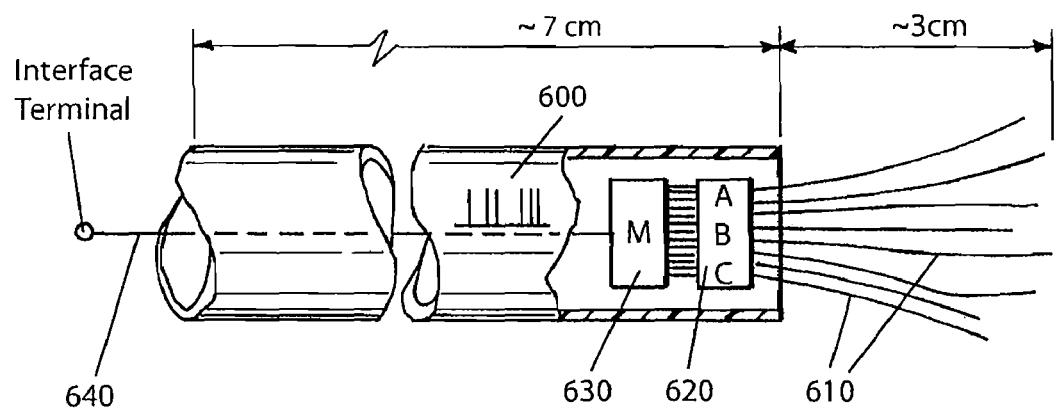
Figure 10C:
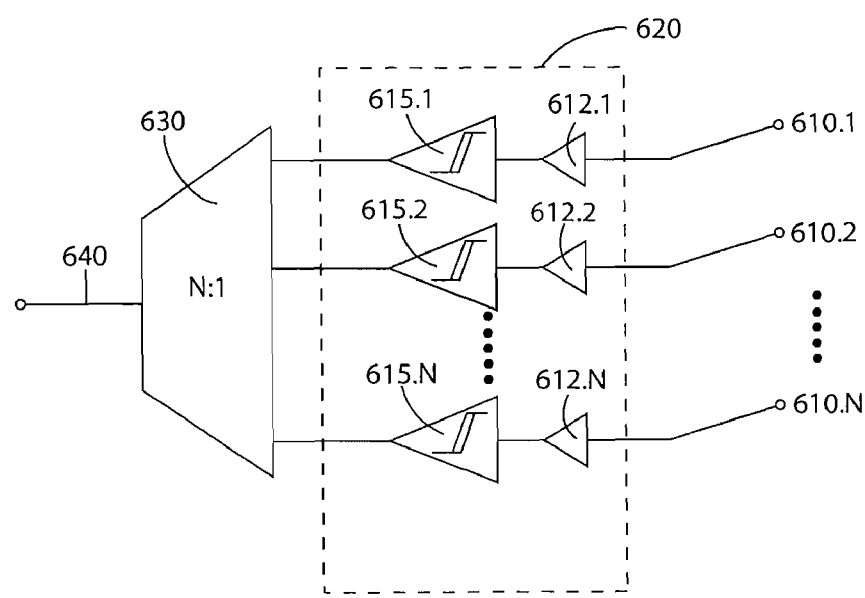
Figure 11:
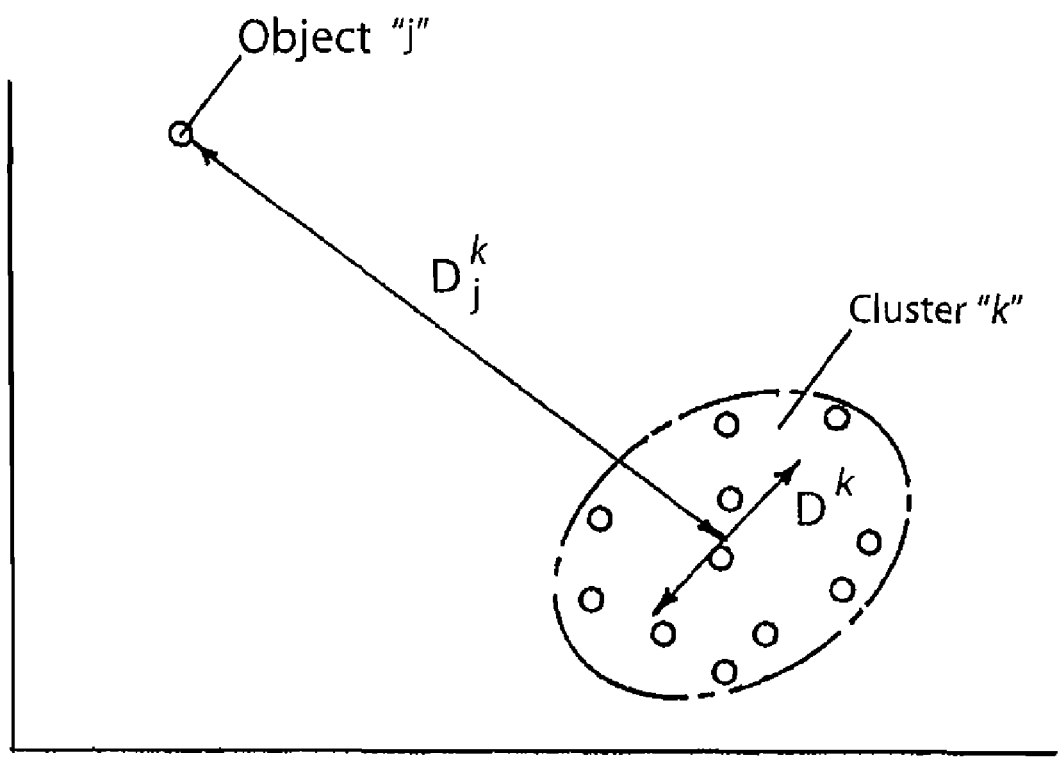
FIG. 11 illustrates the dissimilarity of an object j to a cluster k and the mean dissimilarity within the cluster k.

FIG. 10B is a schematic representation of an exemplary embodiment of a catheter 600 of a brain-machine interface device in accordance with the present invention. A plurality of single nanowire electrodes 610 are coupled to an amplifier/binary converter or analog-digital converter (ADC) 620 which is in turn coupled to a multiplexer (M) 630. As shown in greater detail in FIG. 11C, the ADC 620 can be implemented with an amplifier 612.1-612.N and a Schmitt trigger 615.1-615.N for each of the N nano-wire electrodes 610.1-610.N. Each Schmitt trigger transforms the action potential from the respective amplifier into a pulse train having a binary value (HIGH/LOW or 1/0). As such, at any given instant, only one bit is required to represent the action potential on each nano-wire electrode.

In an exemplary embodiment, each electrode has a diameter of approximately 0.1 μm and a length of 30 mm or less and the micro-wire is approximately one meter long. A single catheter may carry one or more arrangements. In this way, a small number of inexpensive and robust microwires can be used along the catheter length to convey data from a much larger number of nanowire electrodes.

The nanowires are preferably of different lengths so as to position electrodes at different points along the vessels in which they are deployed. Preferably, the nanowires can be used as actuators and steered between various points near the deployed points. The circuitry is preferably located in or proximate to the tip of the catheter so as to minimize the length of the nanowires and to thus optimize noise performance. The circuitry is also preferably implemented with integrated circuit technology in order to fit in the limited space available in or proximate to the tip of the catheter. Prior to deployment, the nanowires are coiled-up within a compartment at the tip of the catheter. As the compartment is opened (e.g., mechanically like a trap door) the electrodes deploy and extend along the vessels, carried by the blood flow and branching out along the branching vessels.

In addition to the hardware-related aspects described above, the present invention also provides the software methods for reading, storing and contextualizing the enormous amount of neuronal information that is provided by the above-described vascular apparatus. Such processing helps provide an understanding of neuronal activity, thereby providing a significant window into brain function, further defining the relations between electrophysiology and the cognitive/motor properties of the brain. The methods of the present invention include signal processing capable of classifying brain states based on neuronal unit activity and field potential analysis. The present invention also provides a package of algorithms and a computational toolkit that is appropriate and effective for data analysis and decision making.

The present invention provides software methods for classifying brain states based on neuronal unit activity and field potential analysis. A goal of such methods is to correlate, in real time, the moment-to-moment electrical activity of neurons with large functional brain states. It is assumed that the electrical properties of neurons define all possible brain states and that such states co-vary systematically with the global state dynamics. However, this does not imply that there exists one-to-one correspondence between purely local patterns of brain activity and a particular set of functional states. Physically, the generation of a new functional state in the brain, for instance the transition "sleep-wakefulness," corresponds to activity reorganization in many groups of neurons. There are practically an infinite number of possible patterns, each slightly different from the other. The approach is to map the small variance patterns into relatively small sets of different functional states. For example, in the simplest case only three global functional states may be considered: 1) sleep, 2) wakefulness, and 3) "none of the above" or uncertain state, e.g., drowsy. The last state is required in order to close the output domain of a mathematical algorithm, since otherwise it would not be possible to solve correctly for any possible input pattern, including the unavoidable impact of noise. Moreover, the third state is vital from a conceptual viewpoint as for instance, to see or not to see light is possible in the awake state only and, hence, during sleep this state could be uncertain.

As mentioned above, an exemplary embodiment of a computational algorithm in accordance with the present invention detects alterations in brain activity that relate to a global change of states. This activity is represented by the set of binary time series taken from many neurons, i.e., by spatiotemporal patterns. The problem is then one of pattern classification, as discussed below. For an algorithm to be useful it must be optimized to: 1) determine the minimal number of hypotheses (possible functional states) concerning the data set; 2) economize on data storage and subsequent data manipulation/calculation; 3) scale for increasing data sets and for the number of functional states; and 4) be robust. In an exemplary embodiment, the present invention provides a method based on a cluster analysis approach.

In the first step, a data set comprising all action potentials over a given time interval is split into J short time intervals by shifting a time window of length T. The time scale T can be varied for different purposes and the choice of a particular T value is a compromise between speed and reliability in data analysis. Each window will be referred to as "an object" or entity assuming that a window encompasses an unchanged functional state. Assuming a correct set of hypotheses concerning the number of clusters, K, (e.g., for three global functional states K=3: wakefulness, sleep, and uncertain state), the J different objects must be related to K functional states.

The algorithm starts with K random clusters, and then moves objects between those clusters in order to assign objects to clusters such that the variance within each cluster would be minimal, while the variance between clusters would be maximal. To implement this function, a measure of dissimilarity between objects is obtained. This can be determined by calculating Euclidean distances between objects in a multi-dimensional space. The average dissimilarity of object j to cluster k (i.e., the distance between j and k) and the average dissimilarity within cluster k are shown in FIG. 12. This algorithm works well under the assumption that the correct dissimilarity has been measured. For time series objects, in the simplest case, neuronal firing rates can be used as coordinates in a multi-dimensional space. Other possible measures, which may be useful in classifying fine functional states such as cognition, includes a dissimilarity matrix based on cross-correlation sums.

The classification algorithm may be referred to as "unsupervised." It is based on the hypothesis of a "good" dissimilarity measure and does not include any optimization. This approach can be upgraded to a supervised training data set, where the correct results of classification are known a priori for a portion of the data and may be used as a feedback reference for improvement of computational speed and reliability. Even after tuning, however, the algorithm may fail because brain plasticity may occur. Thus, the possibility of sudden mistakes may be corrected by means of feedback.

One problem to be solved is the non-stationary nature of brain function. This seems at first glance to be a significant obstacle for any analysis. However, a detailed study of the problem indicates that all functional states are temporal and have essentially different time scales. For example, being awake can last for hours, while cognition can be as short as tens of milliseconds. Furthermore, it is possible to assume that only a limited number of functional states can coexist. These two considerations allow building a new adaptive algorithm capable of discriminating, in principle, any possible functional states.

There are three main parameters at play: 1) the length of the time window, T; 2) the number of clusters of objects, K, being separated; and 3) the dissimilarity measurement. The process of classification can be started with relatively long T, and small K. Thus fast processes (functional states) would be eliminated due to averaging over a protracted time. Moreover, functional states with intermediate time scale and with a strong influence on others would be left out due to very rough classification, since the patterns have been split into a small number of clusters. Then, when a first approximation of cluster boundaries is determined and it can reliably detect functional states of the top level, a step down can be taken by decreasing window size T, and by including finer functional states (increasing K). Moreover, it is possible to work "within" a functional state of the upper level and reject all non-fitting objects. Such a modification of the algorithm allows scalability and a method of exploration of all possible functional states. It should be noted that the deeper the process progresses into the functional state hierarchy, the more complex the computation needed. However, the main parts of the algorithm can be easily paralleled and hence effectively performed by parallel computers or other known processors.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are to some degree approximate, and are provided for purposes of description.

The invention claimed is:

1. A system for transmitting electrical signals to a biological target using vascular-based probes, said system comprising:
a plurality of conducting polymer nanowires, each nanowire having a distal end and a proximal end, and an associated probe portion located at the distal end of each nanowire;
the plurality of conducting polymer nanowires being introduced directly into a vascular territory to which signals are transmitted; wherein the distal end of at least one of the plurality of conducting polymer nanowires is selectively deflectable, thereby allowing at least one of controlled directing of electrical current to a particular area for stimulation and controlled guiding of the polymer nanowires introduced directly into and within the vascular area; and
an electronic interface circuit in electrical communication with the plurality of conducting polymer nanowires, said electronic interface circuit comprising an interface module for interfacing the conducting polymer nanowires with a microwire located in the vicinity of the proximal ends of the conducting polymer nanowires.

2. The system of claim 1 further comprising:
a catheter for delivering said plurality of conducting polymer nanowires directly into the vascular territory; and
a signal processor, the signal processor being arranged in the catheter and being in electrical communication with the plurality of nanowires.

3. The system of claim 1 wherein the conducting polymer nanowires are each characterized by a longitudinal conductivity and a radial conductivity, wherein the longitudinal conductivity is at least five orders of magnitude greater than the radial conductivity.

4. The system of claim 1, wherein the electrical signals received from the biological target are provided as input to a computing device in order to thereby control the computing device.

5. The system of claim 1, wherein the conducting polymer nanowires each comprise a polymer fiber coated with a conductive material.

6. The system of claim 1, wherein the conducting polymer nanowires are produced by slicing a conducting polymer film sandwiched between layers of a frozen liquid.

7. The system of claim 1, wherein the nanowires have different lengths.

8. The system of claim 1, wherein the conducting polymer nanowires are produced using one of a core-shell electrospinning process and a fiber drawing technique.

9. The system of claim 1, wherein the biological target includes the cochlea.

10. The system of claim 1, wherein the biological target includes a limb.

11. The system of claim 1, wherein the transmitted signals are associated with a prosthetic limb.

12. The system of claim 1, wherein at least one conducting polymer nanowire further comprises an insulator, wherein the insulator is removed at the distal region of at least one conducting polymer nanowire and the distal region where the insulator is removed is further provided with an added material which modifies the properties of the nanowire.

13. The system of claim 12, wherein the added material is characterized by one of a higher conductivity than the conducting polymer and a different affinity to a second material relative to the affinity of the polymer to the second material.

14. The system of claim 13, wherein the distal region where the insulator is removed is subjected to an electrochemical dip or growing process to add a second layer of material to the distal region, wherein the second layer of material includes metal.

15. The system of claim 14, wherein the second layer of material includes one of platinum and silver.

16. The system of claim 1, further comprising:
an additional conducting polymer nanowire on the neural tissue proximate to at least one of the plurality of conducting polymer nanowires; said additional conducting polymer nanowire being used to apply a stimulus to the neural tissue;
a circuit for monitoring a further signal on the additional nanowire after applying the stimulus to the neural tissue; and comparing the stimulus signal to the further signal.

17. The system of claim 1 further comprising:
a second conducting polymer nanowire positioned in a second blood vessel proximate to the neural tissue, said second nanowire being of sufficiently small size such that it is capable of being inserted into a capillary; and
a circuit for providing a stimulation signal to said second nanowire.

18. The system of claim 1 further comprising:
a second nanowire being positioned in a second blood vessel proximate to the neural tissue, said second nanowire being of sufficiently small size such that it is capable of being inserted into a capillary; wherein said second nanowire is provided with a monitor signal.

19. The system of claim 1 further comprising:
a filter for filtering the signals from said nanowire;
a processor for classifying brain states based on one of neuronal unit activity and field potential analysis, wherein said processor is operative to correlate electrical activity of neurons with brain states and to perform pattern classification to determine brain states.

* * * * *